US012778587B2

(12) United States Patent
Ma et al.

(10) Patent No.: US 12,778,587 B2
(45) Date of Patent: Nov. 3, 2026

(54) ASYMMETRIC ANASTOMAT WITH ANTI-REFLUX EFFECT FOR ESOPHAGOGASTRIC ANASTOMOSIS

(71) Applicant: HUAI'AN JINOU MEDICAL BIOTECHNOLOGY CO., LTD, Jiangsu (CN)

(72) Inventors: Erhong Ma, Jiangsu (CN); Junling Ma, Jiangsu (CN)

(73) Assignee: HUAI'AN JINOU MEDICAL BIOTECHNOLOGY CO., LTD, Jiangsu (CN)

( * ) Notice: Subject to any disclaimer, the term of this patent is extended or adjusted under 35 U.S.C. 154(b) by 166 days.

(21) Appl. No.: 18/550,959

(22) PCT Filed: May 18, 2023

(86) PCT No.: PCT/CN2023/095001
§ 371 (c)(1),
(2) Date: Sep. 16, 2023

(87) PCT Pub. No.: WO2023/186185
PCT Pub. Date: Oct. 5, 2023

(65) Prior Publication Data
US 2025/0032118 A1 Jan. 30, 2025

(30) Foreign Application Priority Data
Mar. 30, 2022 (CN) ......................... 202210320920.6

(51) Int. Cl.
*A61B 17/11* (2006.01)
*A61B 17/072* (2006.01)
*A61B 17/115* (2006.01)

(52) U.S. Cl.
CPC ........ *A61B 17/1114* (2013.01); *A61B 17/072* (2013.01); *A61B 17/1152* (2013.01);
(Continued)

(58) Field of Classification Search
CPC ............... A61B 17/1114; A61B 17/115; A61B 17/1152; A61B 17/1155; A61B 17/068;
(Continued)

(56) References Cited

U.S. PATENT DOCUMENTS 5,360,154 A 11/1994 Green
2003/0018236 A1* 1/2003 Adams ............... A61B 1/00071 600/128
(Continued)

FOREIGN PATENT DOCUMENTS

CN 1859874 A 11/2006
CN 206548561 U 10/2017
(Continued)

*Primary Examiner* — Diane D Yabut
(74) *Attorney, Agent, or Firm* — SALIWANCHIK, LLOYD & EISENSCHENK

(57) ABSTRACT

The present invention discloses an asymmetric anastomat with anti-reflux effect for esophagogastric anastomosis, the improvements lie in that the end face of a nail bin is formed by two arc-shaped plates that are bent towards the same direction and connected and closed in an end-to-end manner to form an arc-shaped cavity, nail outlet holes in the arc-shaped plates are provided around the arc-shaped cavity, and a cutter is consistent with the arc-shaped cavity in shape and is attached to the edge of the inner side wall of the arc-shaped cavity; a stapling anvil plate on the bottom face of the nail abutting base is formed by working out a cutting groove in a circular plate, the shape of the cutting groove is consistent with the shape of the arc-shaped cavity in the end face of the nail bin, and nail abutting grooves that match the nail outlet holes in position and shape are formed in the stapling anvil plate. After anastomosis with the asymmetric anastomat for esophagus and stomach in the present invention, redundant esophageal and gastric tissues on the anterior wall are deformed into the stomach to form a tongue piece by suturing to a seromuscular layer, and, in conjunction with
(Continued)

manual folding and suturing at the posterior wall, valvula-like tongue pieces that are closed towards each other are formed in the stomach cavity, so that a valvula-like structure is formed together. The anastomotic stoma passage is in a valvula-like closed state when no food is eaten, and the anastomotic stoma is opened due to the peristalsis pressure of the esophagus and an expansion effect of a food mass during eating, so that a cardia-like effect of preventing stomach-esophageal reflux is achieved.

7 Claims, 9 Drawing Sheets
(4 of 9 Drawing Sheet(s) Filed in Color)

(52) U.S. Cl.
CPC ............... *A61B 2017/07257* (2013.01); *A61B 2017/07285* (2013.01)

(58) Field of Classification Search
CPC ........ A61B 17/072; A61B 2017/07257; A61B 2017/07285; A61B 2017/07271; A61B 2017/07278; A61B 2017/1117; A61B 2017/1157; A61B 2017/07221
See application file for complete search history.

(56) References Cited

U.S. PATENT DOCUMENTS

| | | | | |
|---|---|---|---|---|
| 2011/0011916 | A1 | 1/2011 | Levine | |
| 2015/0060525 | A1* | 3/2015 | Vestweber | A61B 17/115 227/180.1 |

FOREIGN PATENT DOCUMENTS

| | | | |
|---|---|---|---|
| CN | 215688164 | U | 2/2022 |
| CN | 114601519 | A | 6/2022 |
| CN | 218899549 | U | 4/2023 |
| WO | 2004110285 | A1 | 12/2004 |

* cited by examiner

ASYMMETRIC ANASTOMAT WITH ANTI-REFLUX EFFECT FOR ESOPHAGOGASTRIC ANASTOMOSIS

CROSS REFERENCE TO RELATED APPLICATIONS

This application is a National Stage of International Application No. PCT/CN2023/095001, filed on May 18, 2023, which claims priority to Chinese Patent Application No. 202210320920.6, filed on Mar. 30, 2022; both of which are hereby incorporated by reference in their entireties.

TECHNICAL FIELD

The present invention relates to the field of medical equipment, in particular to a novel asymmetric anastomat with anti-reflux effect for esophagogastric anastomosis.

BACKGROUND ART

A medical anastomat is a device that is applied to replace manual suturing. The main working principle of an anastomat is to sever and staple tissues for anastomsis, similar to a stapler. For cardia and gastric fundus tumors and esophageal tumors, after surgical resection of the esophagus, cardia or part of gastric tissues at the tumor site, the healthy esophagus and stomach are connected by means of an anastomat to restore the continuity of the digestive tract. At present, a circular anastomat or a linear cutting and suturing device is usually used clinically. After anastomosis, the esophagus is directly in communication with the stomach, and the anastomotic stoma is in a persistently open state, losing a cardia-like structure and anti-reflux effect. Consequently, intractable reflux esophagitis occurs after the operation, which seriously affects the quality of life of the patient.

SUMMARY OF THE INVENTION

In view of the shortcomings in the prior art, an object of the present invention is to provide an asymmetric anastomat with anti-reflux effect for esophagogastric anastomosis to solve the above-mentioned problem, with which, through arc-shaped asymmetric stapling and ring cutting, the tissues at the anterior wall of the anastomotic stoma are elastically deformed and project toward the stomach cavity, while the esophagus and the seromuscular layer of the stomach, which are at the posterior wall of the anastomotic stoma, are further folded, sutured and trimmed so as to form a valvula-like structure at the anastomotic stoma. The valvula-like structure is in a closed state when no food is eaten, thus, it has a certain anti-reflux effect.

To attain the object described above, the present invention provides the following technical solution:

An asymmetric anastomat with anti-reflux effect for esophagogastric anastomosis, comprising:

- a gun body;
- an adjusting mechanism arranged along the length direction of the gun body and penetrating through the gun body, a turning handle arranged at the rear end is transmissingly connected to a guide shaft at the front end;
- a nail abutting base arranged at the distal end of the adjusting mechanism, having a stapling anvil shaft that can be snap-fitted with the guide shaft, wherein the movement of the nail abutting base in the length direction of the gun body is adjusted by means of the adjusting mechanism;
- an anastomotic cutting mechanism arranged on the front part of the gun body, comprising a nail bin for storing suturing nails and a nail pushing plate inside the nail bin, and a cutter that is arranged adjacent to the inner side of the nail bin;
- an actuating mechanism arranged inside the gun body and configured to push and connect the nail pushing plate and the cutter to cooperate with the nail abutting base to accomplish stapling and ring cutting;
- an end face of the nail bin is formed by two arc-shaped plates that are bent towards the same direction and connected and closed in an end-to-end manner to form a central arc-shaped cavity and; the arc-shaped plate is provided with nail outlet holes that are arranged in at least two circles around the arc-shaped cavity;
- a stapling anvil plate arranged on the bottom face of the nail abutting base is formed by working out a cutting groove matching the arc-shaped cavity in the end face of the nail bin in shape in a circular plate, and nail abutting grooves that match the nail outlet holes in position and shape are formed in the stapling anvil plate; and
- the cutter is consistent with the arc-shaped cavity in the end face of the nail bin in shape and is attached to the edge of the inner side wall of the arc-shaped cavity.

In a further improved technical solution of the present invention, the stapling anvil shaft of the nail abutting base comprises an arc-shaped plate and a snap-fitting cylinder, wherein the arc-shaped plate is connected inside the cutting groove and has the same arc orientation as the cutting groove, a suture hole is formed in the arc-shaped plate, and the top end of the snap-fitting cylinder is connected to the bottom end of the arc-shaped plate. The bottom end of the esophagus is purse-sutured and fixed to the nail abutting base via the suture hole in the arc-shaped plate, thereby the suturing scam is more compliant.

In a still further improved technical solution of the present invention, the circumferential wall of the snap-fitting cylinder is provided with a longitudinal hole, an elastic plate is arranged inside the longitudinal hole, a clamping groove is arranged in the guide shaft, the guide shaft penetrates into the snap-fitting cylinder, and the elastic plate deforms with an snap-fitting protrusion on its inner wall snap-fitted in the clamping groove so that the snap-fitting cylinder is snap-fitted and fixed to the guide shaft. Thus, the connection is firm and easy to disconnect.

In a still further improved technical solution of the present invention, at least two rows of nail outlet holes are arranged in the end face of the nail bin, forming an inner circle and an outer circle, and each row of nail outlet holes is arranged in a staggered manner from the other rows of nail outlet hole, thereby nail outlet circles are formed without clearance. Thus, the anastomsis is tight and compact, without any gap.

In a still further improved technical solution of the present invention, a cutter anvil is arranged on the peripheral wall of the cutting groove of the stapling anvil plate. The incision is neat since the cutter abuts against the cutter anvil when it cuts the tissues.

In a still further improved technical solution of the present invention, at least one positioning protrusion is arranged on the peripheral wall of the guide shaft or the inner wall of the stapling anvil shaft, and a positioning groove is arranged in the inner wall of the corresponding snap-fitted stapling anvil shaft or the peripheral wall of the corresponding snap-fitted guide shaft. Thus, circumferential rotation and deformation is prevented when the nail abutting base and the nail bin are snap-fitted.

In a further improved technical solution of the present invention, the actuating mechanism comprises a push rod inside the gun body and an actuating handle hinged to the lower part of the handle base of the gun body, the front end of the push rod is connected to the nail pushing plate and the cutter, and the rear end of the push rod is connected to the actuating handle.

Beneficial Effects

When the digestive tract is reconstructed during the operation, the front section of the gun body of the asymmetric anastomat in the present invention is extended into the stomach cavity, the guide shaft of the asymmetric anastomat is led out from the anterior wall of the stomach, the nail abutting base is placed in the lower end of the esophagus, the bottom end of the esophagus is purse-sutured and tightened, the arc-shaped concave surface of the anastomotic stoma is adjusted to be located at the anterior wall of the stomach, and anastomosis is performed after the stapling anvil shaft and the guide shaft are snap-fitted and tightened after rotation. (1) After the anastomosis, the redundant tissues of esophagus and stomach stapled at the anterior wall of the anastomotic stoma are elastically deformed and project into the gastric cavity due to seromuscular suturing, forming tongue pieces protruding obliquely downward to the opposite side; at the same time, the posterior wall of the anastomotic stoma is deformed and displaced upward and forward, and the arc-shaped anastomotic edges on the two sides are at relative upper and lower positions, and they are deformed and get close to each other, so that the anastomotic stoma tends to close; (2) then, the esophagus and the seromuscular layer at the proximal cutting end of the stomach, which are at the posterior wall of the anastomotic stoma, are manually folded, sutured and trimmed, so that the folded part of the stomach wall forms a valvula-like structure at the posterior wall of the anastomotic stoma in the stomach cavity, and pushes the posterior wall to deform reversely in an arc shape and get close to the anterior wall of the anastomotic stoma; through the combined action of the two, a valvula-like structure like the "His flap-valve" of cardia is formed at the reconstructed anastomotic stoma, thereby the circular hole-like unobstructed communication state caused by anastomosis with an ordinary circular anastomat is changed; in a rest state, the reconstructed valvula-like structure is in a closed state; during stomach peristalsis and contraction, the internal pressure of the stomach increases, and the gastric content and the expanded fundus of stomach push the "His flap-valve" further to the anterior wall of the esophagus at the anterior wall of the anastomotic stoma, so that it is closed more tightly to prevent the gastric content from flowing back to the esophagus, thereby a certain anti-reflux effect is achieved. During eating, under the peristaltic pressure of the esophagus and the expansion action of the food mass, the arc-shaped "His flap-valve" at the reconstructed anastomotic stoma is elastically deformed in a circular shape and opens to the stomach cavity at the distal end, without affecting eating.

DESCRIPTION OF DRAWINGS

The patent or application file contains at least one drawing executed in color. Copies of this patent or patent application publication with color drawings(s) will be provided by the Office upon request and payment of the necessary fee.

FIG. 10 shows the effect of an asymmetric esophagogastrostomy by manual suturing to simulate the structural principle of the present invention, in which.

Figure 1:
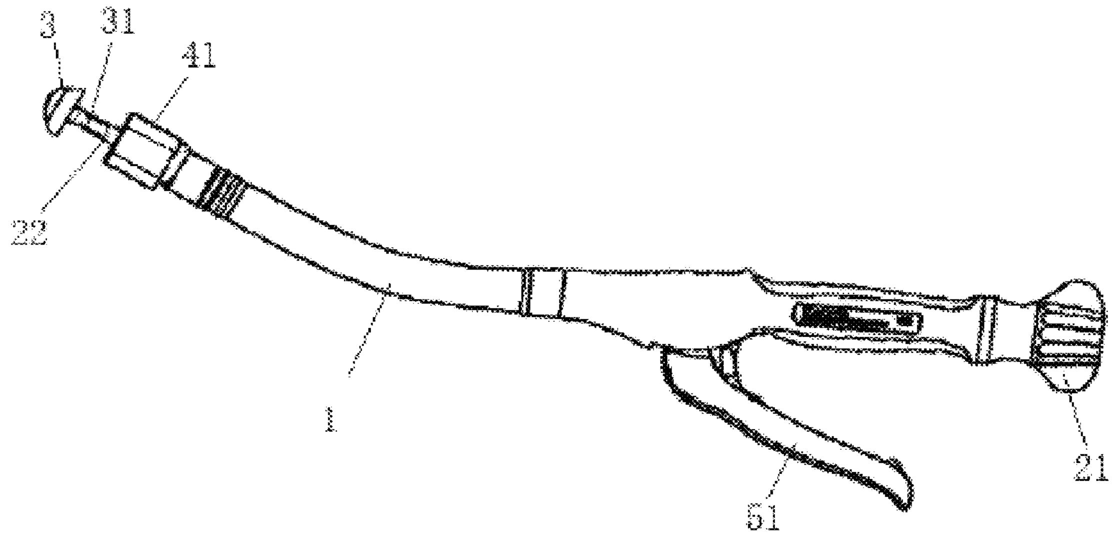
FIG. 1 is a schematic structural diagram of the overall appearance of the asymmetric anastomat for esophagus and stomach with an anti-reflex effect in the present invention.
Figure 2:
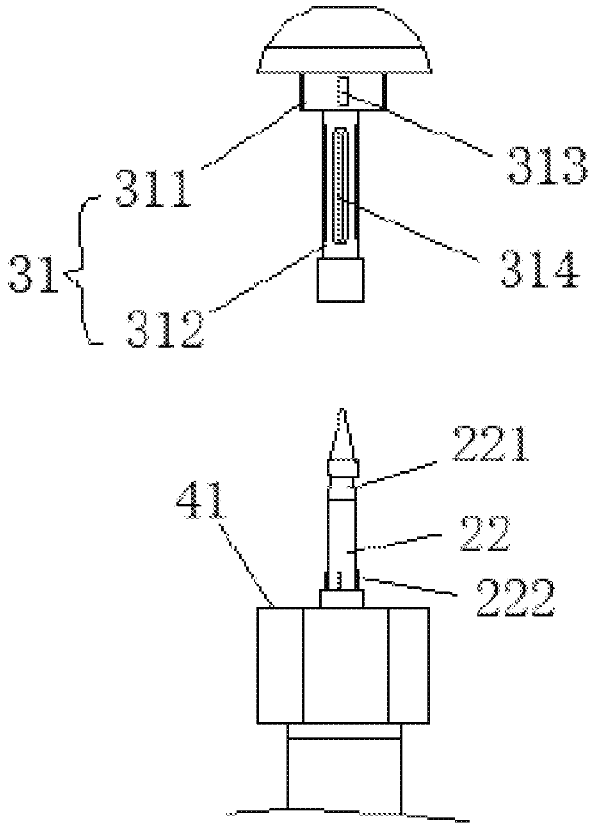
FIG. 2 is a partial front view of the asymmetric anastomat for esophagus and stomach with an anti-reflex effect in the present invention when the nail abutting base at the front end is separated.
Figure 3:
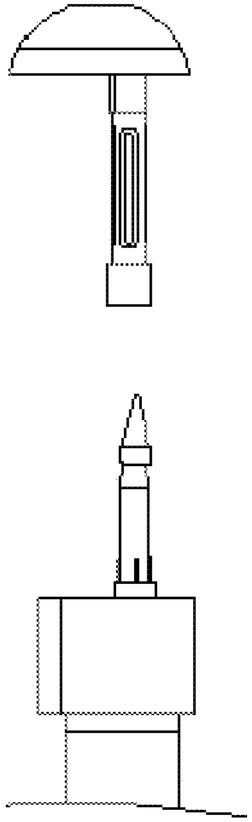
FIG. 3 is a partial side view of the asymmetric anastomat for esophagus and stomach with an anti-reflex effect in the present invention when the nail abutting base at the front end is separated.
Figure 4:
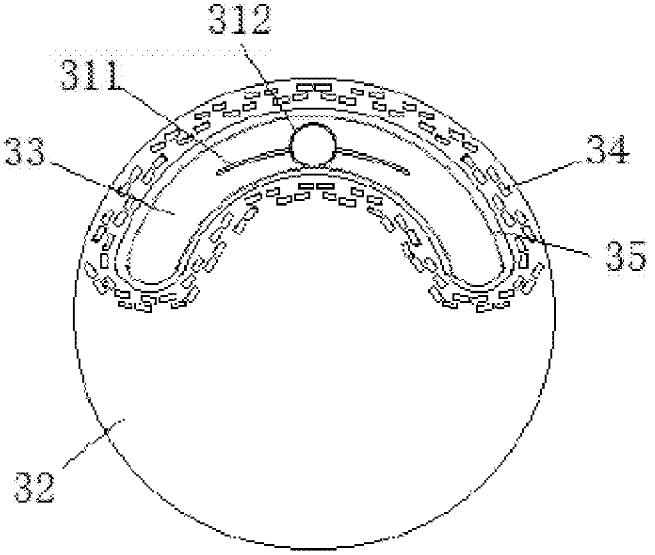
FIG. 4 is a bottom view of the bottom surface of the nail abutting base in the present invention.
Figure 5:
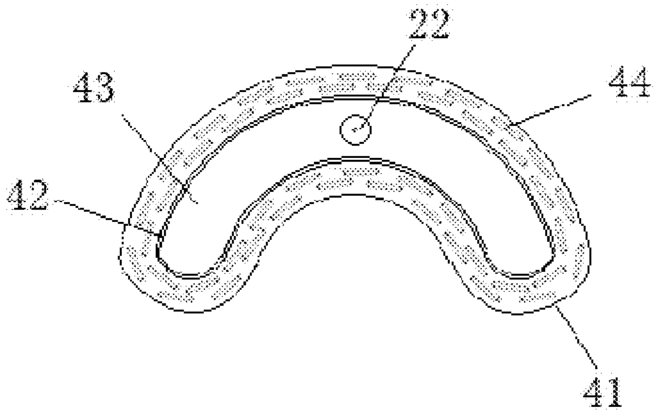
FIG. 5 is an end view of the nail bin in the present invention.

In the figures: 1—gun body, 3—nail abutting base, 21—turning handle at rear end, 22—guide shaft, 221—clamping groove, 222—positioning protrusion, 31—stapling anvil shaft, 32—stapling anvil plate, 33—cutting groove, 34—nail abutting groove, 35—cutter anvil, 311—arc-shaped plate, 312—snap-fitting cylinder, 313—suture hole, 314—elastic plate, 41—nail bin, 42—cutter, 43—arc-shaped cavity, 44—nail outlet hole, 51—actuating handle, 52—safety mechanism, 6—first tongue piece, 7—second tongue piece, A—anterior wall, B—posterior wall, C—cutting end, D—fundus of stomach.

EMBODIMENTS

The technical solution of the present invention will be described in detail below with reference to the accompanying drawings. As shown in FIGS. 1-5:

- a gun body 1;
- an adjusting mechanism arranged along the length direction of the gun body 1 and penetrating through the gun body 1, a turning handle 21 at rear end is transmissingly connected to a guide shaft 22 at the front end;
- an anastomotic cutting mechanism arranged on the front part of the gun body, comprising a nail bin 41 for storing suturing nails and a nail pushing plate (not shown in figures) inside the nail bin 41, and a cutter 42; wherein an end face of the nail bin 41 is formed by two arc-shaped plates 311 that are bent towards the same direction and connected and closed in an end-to-end manner to form a central arc-shaped cavity 43, and the arc-shaped plate 311 is provided with nail outlet holes 44 arranged in a circle around the arc-shaped cavity 43; the cutter 42 is consistent with the arc-shaped cavity 43 in the end face of the nail bin 41 in shape and is attached to the edge of the inner side wall of the arc-shaped cavity 43;

at least two rows of nail outlet holes 44 are arranged in the end face of the nail bin 41, forming an inner circle and an outer circle, and the two rows of nail outlet holes 44 are arranged in a staggered manner from each other, thereby nail outlet circles are formed without clearance.

A nail abutting base 3 is arranged at the distal end of the adjusting mechanism, a stapling anvil plate 32 on the bottom surface of the nail abutting base 3 is formed by working out a cutting groove 33 in a circular plate, the shape of the cutting groove 33 is consistent with the shape of the arc-shaped cavity in the end surface of the nail bin, nail abutting grooves 34 that match the nail outlet holes 44 in position and shape are arranged in the stapling anvil plate around the cutting groove 33, and a plastic cutter anvil 35 is arranged on the peripheral wall of the cutting groove 33, and the plastic cutter anvil 35 matches the cutter 42 in shape. A stapling anvil shaft 31 is arranged in the cutting groove 33, and the stapling anvil shaft 31 comprises an arc-shaped plate 311 and a snap-fitting cylinder 312, the arc-shaped plate 311 is connected in the cutting groove 33 and has the same arc orientation as the cutting groove 33, the top end of the snap-fitting cylinder 312 is connected to the bottom end of the arc-shaped plate 311, a vertical hole is formed in the peripheral wall of the snap-fitting cylinder 312, an elastic plate 314 is arranged in the vertical hole, a clamping groove 221 is formed in the guide shaft 22 of the adjusting mechanism, the guide shaft 22 penetrates through the snap-fitting cylinder 312 and fits therein, the elastic plate 314 deforms with a snap-fitting protrusion on its inner wall clamped in the clamping groove 221 so that the stapling anvil shaft 31 are snap-fitted and fixed to the guide shaft 22, and the movement of the nail abutting base 3 in the length direction of the gun body 1 is adjusted by means of the adjusting mechanism; at least one positioning protrusion 222 is arranged on the inner wall of the stapling anvil shaft 31, and a positioning groove (not shown in figures) is arranged in the peripheral wall of the guide shaft which is correspondingly snap-fitted with the protrusion; when the positioning protrusion is snap-fitted with the positioning groove, the stapling anvil shaft 31 and the guide shaft 22 cannot rotate and displace. A suture hole 313 is formed in the arc-shaped plate 311, the bottom end of the esophagus is purse-sutured and closed, the two ends of the suture line pass through the arch back side of the suture hole 313 respectively, run around the arc-shaped plate 311 in the reversed direction, and are fastened at the arch back portion of the arc-shaped plate 311, so that the tissues at the bottom end of the esophagus tightly abut against the arc-shaped plate 311 and are closed.

An actuating mechanism arranged on the gun body 1 comprises a push rod (not shown in figures) inside the gun body and an actuating handle 51 hinged to the lower part of a handle base of the gun body. The actuating handle is provided with a safety mechanism 52, the front end of the push rod is connected to a nail pushing plate and the cutter 42, and the rear end of the push rod is connected to the actuating handle 51 to push and connect the nail pushing plate and the cutter 42, so as to cooperate with the nail abutting base 3 for stapling and ring cutting.

Figure 6:
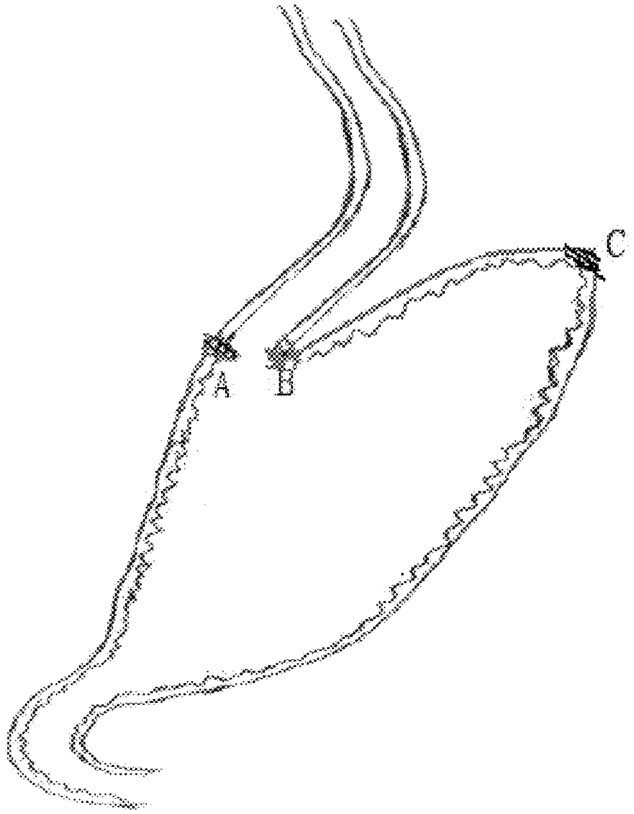
FIG. 6 is a schematic diagram illustrating the state of communication between the esophagus and the stomach that are anastomosed with a conventional circular anastomat.
Figure 9:
FIG. 9 shows the effect of esophagogastrostomy using a conventional circular anastomat.

At present, after surgical resection of the cardia, part of esophagus and/or stomach tissues at the tumor site, a circular anastomat is commonly used for esophagogastrostomy. After anastomosis, the passage between the esophagus and the stomach is an open and unobstructed circular straight passage (as shown in FIG. 6). Consequently, severe gastric juice reflux often occurs after the operation, which seriously affects the quality of life of the patient. FIG. 9 shows the effect of esophagogastrostomy using a conventional circular anastomat.

Figure 7:
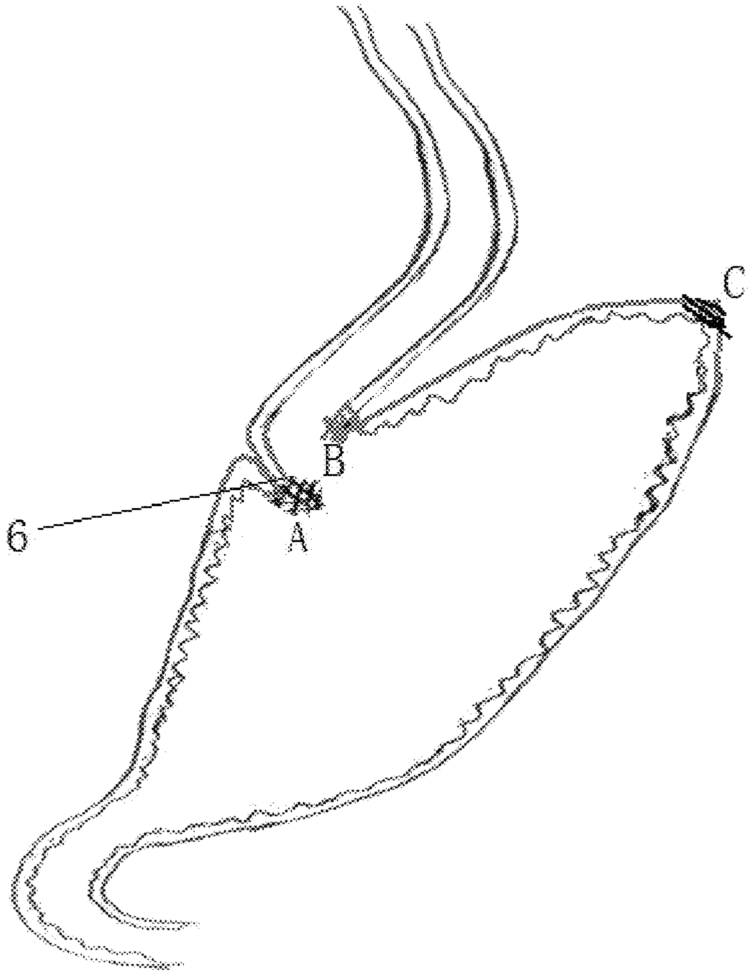
FIG. 7 is a schematic diagram illustrating the state of communication between the esophagus and the stomach after asymmetric anastomosis in the present invention.
Figure 8:
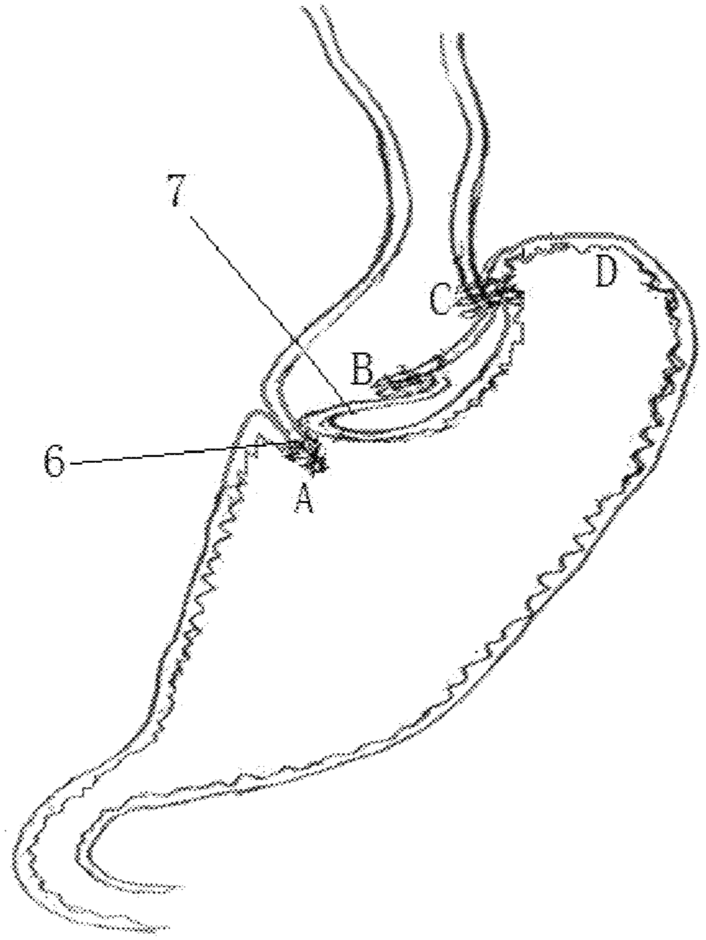
FIG. 8 is a schematic diagram illustrating the state of communication between the esophagus and the stomach after asymmetric anastomosis is performed and a second tongue piece (valvula-like structure) is formed by suturing and trimming the esophagus and the stomach in the present invention.

The end face of the nail bin 41 of the anastomotic cutting mechanism of the asymmetric anastomat in the present invention is formed by two arc-shaped plates 311 that are bent towards the same direction and connected in an end-to-end manner to form a central arc-shaped cavity 43, and the arc-shaped plate 311 is provided with nail outlet holes arranged in at least two circles around the arc-shaped cavity 43; the stapling anvil plate 32 on the bottom surface of the nail abutting base 3 is formed by working out a cutting groove in the circular plate, the shape of the cutting groove is consistent with the shape of the arc-shaped cavity in the end face of the nail bin 41, nail abutting grooves 34 that match the nail outlet holes of the nail bin 41 in position and shape are formed in the stapling anvil plate 32, and the cutter 42 is consistent with the arc-shaped cavity 43 in the end face of the nail bin 41 in shape and is attached to the edge of the inner side wall of the arc-shaped cavity 43. Thus, after the suturing and anastomsis of the esophageal and gastric tissues, the anastomotic stoma is an arc-shaped ring bent towards the same direction and connected end to end, and then ring cutting is carried out within the arc-shaped ring with the cutter 42, redundant arc-shaped tissues are reserved for the esophagus and stomach on one side of the concave front wall A of the anastomotic stoma after the ring cutting, and the redundant arc-shaped tissues on the side are elastically deformed and extend into the stomach by suturing the seromuscular layer, forming a first tongue piece 6 (as shown in FIG. 7) extending obliquely downward toward the rear wall B (the opposite side), and the edge of the arc-shaped anastomotic stoma on the side of the rear wall B is elastically deformed upward accordingly, and the edges at the front wall A and the rear wall B are located at relative upper and lower positions and tend to get close to each other. Then, the esophagus at one side of the rear wall B of the anastomotic stoma and the stomach near the cutting end C are subject to folding and suturing to the seromuscular layer manually, so that the folded part of the stomach wall forms a valvula-like structure (a second tongue piece 7) in the stomach cavity, and is pushed to the opposite side, so that it is elastically deformed in a reversed arc shape and extends, and two valvula-like structures that are closed towards each other are formed at the anastomotic stoma; the passage here is closed when no food is eaten (as shown in FIG. 8). Thus, the original state of communication through straight circular holes without blockage is changed, a cardia-like anti-reflux effect is achieved, and the fundus of stomach D is constructed as well. During eating, owing to the peristaltic pressure of the esophagus and the expansion of the food mass, the local anastomotic stoma is opened, and doesn't affect the passage of food.

Figure 10A:
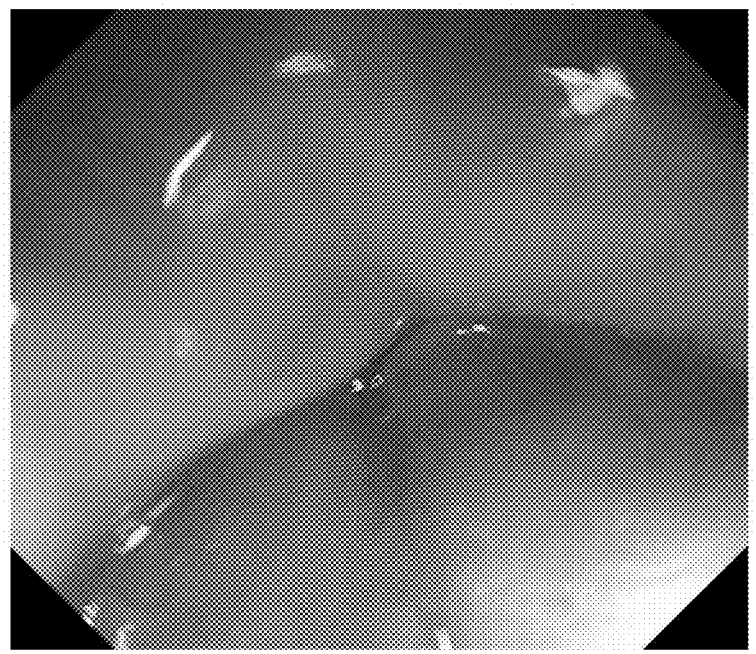
FIG. 10*a* shows a closed arc-shaped valvula-like structure.
Figure 10B:
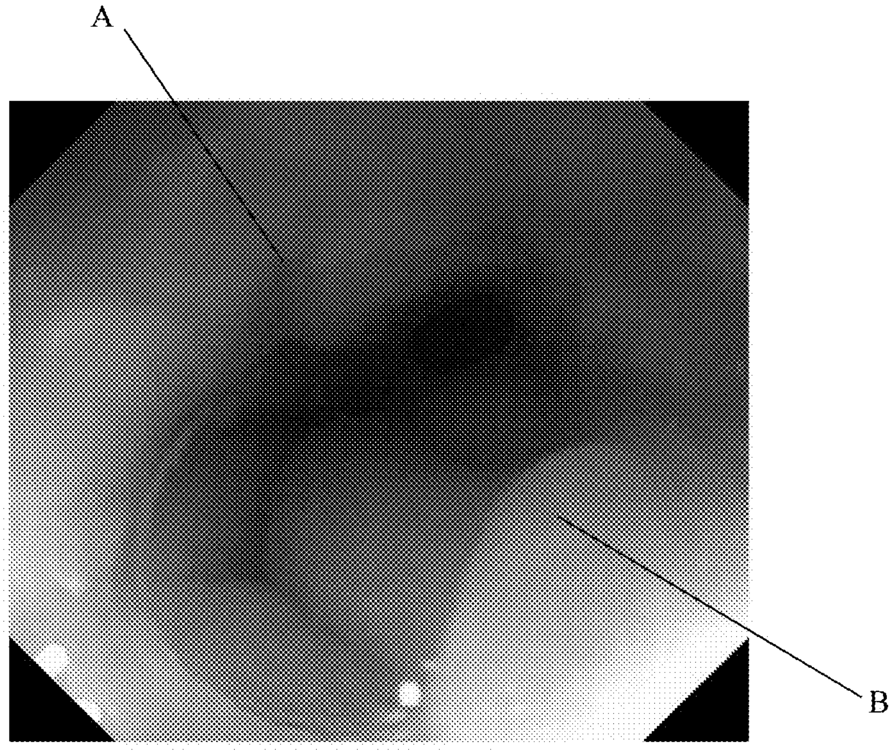
FIGS. 10*b*-10*e* show the deformation from arc-shape to circular cavity.
Figure 10C:
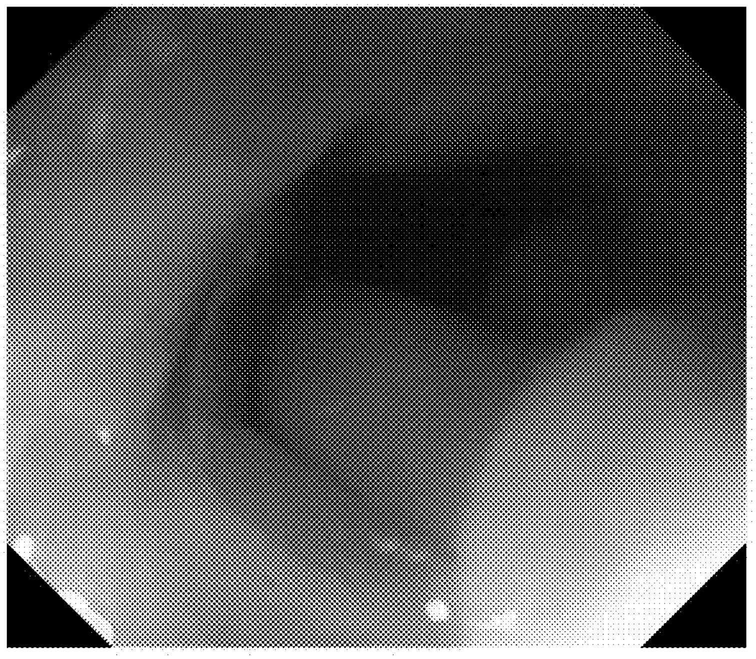
Figure 10D:
Figure 10E:
Figure 10F:
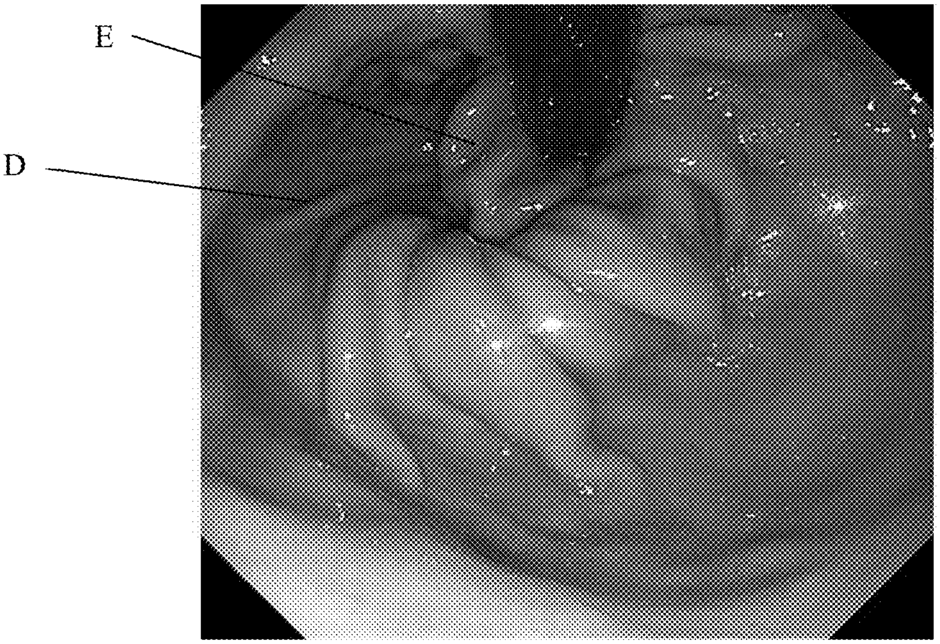
FIG. 10*f* shows the reconstructed fundus of stomach and valvula-like structure thereof.

FIG. 10 shows the effect of asymmetric esophagogastrostomy by manual suturing to simulate the structural principle of the present invention, in which, FIG. 10*a* shows a closed state when no food is eaten; at that point, the anastomotic stoma is a curved seam; FIGS. 10*b*, 10*c*, 10*d* and 10*e* show the dynamic change process when the esophagus is inflated and expanded; wherein FIG. 10*b* shows initial inflation; FIG. 10*c* shows that the anastomotic stoma is in the form of a gradually expanding crescent arc-shaped cavity when inflating; FIG. 10*d* shows that the posterior wall begins to deform elastically in the reversed direction in an arc-shaped manner after persistent inflation, FIG. 10*e* shows that the anastomotic stoma is deformed into a circular cavity after complete inflation, and the consecutive views show that the anastomotic stoma has high expansibility and can avoid stenosis; FIG. 10*f* shows that the peripheral wall of the anastomotic stoma is closely attached to the peripheral wall of a projecting gastroscope when viewed in a direction from the interior of the stomach to the esophagus (inverted position), and the reconstructed valvula-like structure E and the fundus of stomach D can also be seen.

Although some preferred embodiments of the present invention are described above, the scope of protection of the present invention is not limited to the above exemplary embodiments. Any anastomat designed in any shape based on the idea of the present invention to reestablish the continuity of the digestive tract and thereby form an asymmetric structure that has a valvula-like closing effect and certain anti-reflux effect on the two sides of the anastomotic stoma should be deemed as falling in the scope of protection of the present invention. It should be noted that those skilled in the art can make various improvements and modifications without departing from the principle of the present invention, and those improvements and modifications should also be deemed as falling in the scope of protection of the present invention.

The invention claimed is:

1. An asymmetric anastomat with anti-reflux effect for esophagogastric anastomosis, comprising:

a gun body;

an adjusting mechanism arranged along a length direction of the gun body and penetrating through the gun body, a turning handle arranged at a rear end of the adjusting mechanism is transmissingly connected to a guide shaft at a front end of the adjusting mechanism;

a nail abutting base arranged at a distal end of the adjusting mechanism, having a stapling anvil shaft that can be snap-fitted with the guide shaft, wherein the movement of the nail abutting base in the length direction of the gun body is adjusted by means of the adjusting mechanism;

an anastomotic cutting mechanism arranged on a front part of the gun body, comprising a nail bin for storing suturing nails and a nail pushing plate inside the nail bin, a cutter that is arranged adjacent to an inner side of the nail bin and a cutter gasket;

an actuating mechanism arranged inside the gun body and configured to push and connect the nail pushing plate and the cutter to cooperate with the nail abutting base to accomplish stapling and ring cutting;

an end face of the nail bin is formed by two arc-shaped plates that are bent towards the same direction and connected and closed in an end-to-end manner to form a central arc-shaped cavity; the two arc-shaped plates are provided with nail outlet holes that are arranged in at least two circles around the arc-shaped cavity;

a stapling anvil plate on a bottom face of the nail abutting base is formed by working out a cutting groove in a circular plate, the shape of the cutting groove matches the shape of the arc-shaped cavity in the end face of the nail bin, and nail abutting grooves that match the nail outlet holes in position and shape are formed in the stapling anvil plate; and the cutter is consistent with the arc-shaped cavity in the end face of the nail bin in shape and is attached to an edge of the inner side wall of the arc-shaped cavity.

2. The asymmetric anastomat with anti-reflux effect for esophagogastric anastomosis according to claim 1, wherein the stapling anvil shaft of the nail abutting base comprises an arc-shaped plate and a snap-fitting cylinder, wherein the arc-shaped plate is connected inside the cutting groove and has the same are orientation as the cutting groove, a suture hole is formed in the arc-shaped plate, and a top end of the snap-fitting cylinder is connected to a bottom end of the arc-shaped plate.

3. The asymmetric anastomat with anti-reflux effect for esophagogastric anastomosis according to claim 2, wherein a circumferential wall of the snap-fitting cylinder is provided with a longitudinal hole, an elastic plate is arranged inside the longitudinal hole, a clamping groove is arranged in the guide shaft, the guide shaft penetrates into the snap-fitting cylinder and fits therein, and the clastic plate deforms with an snap-fitting protrusion on its inner wall clamped in the clamping groove so that the snap-fitting cylinder is snap-fitted and fixed to the guide shaft.

4. The asymmetric anastomat with anti-reflux effect for esophagogastric anastomosis according to claim 1, wherein at least two rows of nail outlet holes are arranged in the end face of the nail bin forming an inner circle and an outer circle, and the at least two rows of nail outlet holes are arranged in a staggered manner from each other, thereby nail outlet circles are formed without clearance.

5. The asymmetric anastomat with anti-reflux effect for esophagogastric anastomosis according to claim 1, wherein a cutter anvil is arranged on a peripheral wall of the cutting groove of the stapling anvil plate.

6. The asymmetric anastomat with anti-reflux effect for esophagogastric anastomosis according to claim 1, wherein at least one positioning protrusion is arranged on a peripheral wall of the guide shaft or an inner wall of the stapling anvil shaft, and a positioning groove is arranged in an inner wall of the corresponding snap-fitted stapling anvil shaft or the peripheral wall of the corresponding snap-fitted guide shaft.

7. The asymmetric anastomat with anti-reflux effect for esophagogastric anastomosis according to claim 1, wherein the actuating mechanism comprises a push rod in the gun body and an actuating handle hinged to a lower part of a handle base of the gun body, wherein a front end of the push rod is connected with the nail pushing plate and the cutter, and the rear end of the push rod is connected with the actuating handle, and the actuating handle is provided with a safety mechanism.

* * * * *